United States Patent
Ishiguro et al.

(10) Patent No.: US 9,217,726 B2
(45) Date of Patent: Dec. 22, 2015

(54) GAS SENSOR CONTROL APPARATUS

(71) Applicant: NGK SPARK PLUG CO., LTD., Nagoya-shi, Aichi (JP)

(72) Inventors: Yasuhiro Ishiguro, Komaki (JP); Yu Akiyama, Kagamigahara (JP); Tomohisa Terui, Ichinomiya (JP); Kazuhisa Fujibayashi, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 316 days.

(21) Appl. No.: 13/907,248

(22) Filed: May 31, 2013

(65) Prior Publication Data
US 2013/0319857 A1  Dec. 5, 2013

(30) Foreign Application Priority Data
May 31, 2012  (JP) .................... 2012-125403

(51) Int. Cl.
*G01N 27/416* (2006.01)
(52) U.S. Cl.
CPC .................. *G01N 27/4162* (2013.01)
(58) Field of Classification Search
CPC .................................................. G01N 27/416
See application file for complete search history.

(56) References Cited

U.S. PATENT DOCUMENTS

2010/0122568 A1*  5/2010  Inoue et al. .................. 73/31.05
2011/0290015 A1*  12/2011  Ishida et al. ............... 73/335.02

FOREIGN PATENT DOCUMENTS

| DE | 102007043728 A1 | 4/2009 |
| JP | 58-195202 A | 11/1983 |
| JP | 2000-183071 A | 6/2000 |
| JP | 2003-150204 A | 5/2003 |
| JP | 2006-113977 A | 4/2006 |
| JP | 2010-121951 A | 6/2010 |
| JP | 2010-281732 A | 12/2010 |
| JP | 2011-220610 A | 11/2011 |

OTHER PUBLICATIONS

Communication dated Sep. 24, 2014 from the Japanese Patent Office in counterpart application No. 2012-125403.

* cited by examiner

*Primary Examiner* — Jennifer Dieterle
(74) *Attorney, Agent, or Firm* — Sughrue Mion, PLLC

(57) ABSTRACT

A gas sensor control apparatus (1) for a gas sensor (2) including an electromotive force cell (24) and a pump cell (14) includes current control means (69) for feedback-controlling the pump current Ip, voltage setting means S5, S13 for setting a target voltage Vr to either of first and second target voltage Vr1 and Vr2, and constant group setting means S4, S12 for setting a group of feedback control constants to a first group Kpid1 when the target voltage is Vr1 and to a second group Kpid2 when the target voltage is Vr2. The second group Kpid2 is determined such the pump current Ip becomes stable more quickly as compared with the case where the first group of control constants Kpid1 continues to be used.

5 Claims, 6 Drawing Sheets

GAS SENSOR CONTROL APPARATUS

BACKGROUND OF THE INVENTION

1. Field of the Invention

The present invention relates to a gas sensor control apparatus which also detects the H₂O gas concentration of a gas under measurement by using a gas sensor which detects the concentration of a specific gas contained in the gas under measurement.

2. Description of the Related Art

Examples of conventionally known gas sensors for detecting the concentration of a specific gas contained in a gas under measurement, such as exhaust gas discharged from an internal combustion engine, include an oxygen sensor for detecting the concentration of oxygen and an NOx sensor for detecting the concentration of nitrogen oxide (NOx). These gas sensors include a sensor element(s) composed of a solid electrolyte body mainly made of zirconia. For example, a full-range air-fuel ratio sensor whose output changes linearly with oxygen concentration has two sensor elements; i.e., an electromotive force cell and a pump cell. The current flowing between the electrodes of the pump cell is controlled such that the voltage generated between the electrodes of the electromotive force cell becomes constant, and the oxygen concentration is detected from the magnitude of the current flowing through the pump cell.

Patent Document 1 discloses a gas concentration/humidity detection apparatus which detects not only the concentration of a specific gas contained in a gas under measurement, but also the humidity of the gas under measurement. In this gas sensor, the detected concentration of the specific gas (e.g., oxygen concentration) is corrected on the basis of the detected humidity.

In the gas concentration/humidity detection apparatus disclosed in Patent Document 1, when the humidity of the gas under measurement (namely, the concentration of H₂O gas contained in the gas under measurement) is detected, the control target voltage of the electromotive force cell is switched from a first reference voltage (e.g., 450 mV) at which the H₂O gas contained in the gas under measurement does not substantially dissociate, to a second reference voltage (e.g., 1000 mV) at which the H₂O gas contained in the gas under measurement dissociates. The H₂O gas concentration is detected on the basis of first and second currents which are pump currents detected when the first and second reference voltages are used, respectively.

[Patent Document 1] Japanese Patent Application Laid-Open (kokai) No 2010-281732

Problems to be Solved by the Invention

However, after the control target voltage is switched from the first reference voltage to the second reference voltage, it is necessary to wait for a relatively long time (e.g., several to about 10 sec) before the pump current under feedback control becomes stable such that a proper second current can be obtained. Meanwhile, during a period during which the H₂O gas concentration is detected, the oxygen concentration cannot be detected. Therefore, during this period feedback control of air-fuel ratio for an engine using the oxygen concentration output (air-fuel ratio output) of the gas sensor cannot be performed, and the air-fuel ratio is subject to open-loop control. Therefore, there is a need to shorten, to the extent possible, the time required for properly detecting the H₂O gas concentration.

SUMMARY OF THE INVENTION

The present invention has been accomplished in order to solve the above problems, and an object thereof is to provide a gas sensor control apparatus which uses a gas sensor so as to detect the concentration of a specific gas (e.g., oxygen) contained in a gas under measurement and to perform another measurement such as measurement of the concentration of H₂O gas contained in the gas under measurement by changing a target voltage, and which gas sensor apparatus can quickly stabilize feedback-controlled pump current after the target voltage is changed.

The above object of the invention has been achieved by providing (1) a gas sensor control apparatus for detecting the concentration of a specific gas contained in a gas under measurement using a gas sensor which includes an electromotive force cell having an oxygen ion conductive first solid electrolyte body and a pair of first electrodes formed on the first solid electrolyte body, and a pump cell having an oxygen ion conductive second solid electrolyte body and a pair of second electrodes formed on the second solid electrolyte body, the gas sensor control apparatus comprising: current control means for feedback-controlling pump current flowing between the pair of second electrodes such that an electromotive force cell voltage produced between the pair of first electrode becomes equal to a target voltage; voltage setting means for setting the target voltage to either of a first target voltage when the concentration of the specific gas is detected and a second target voltage different from the first target voltage; and constant group setting means for setting a group of control constants used for the feedback control to a first group of control constants when the target voltage is the first target voltage and to a second group of control constants when the target voltage is the second target voltage, wherein at least one of the second group of control constants differs from a corresponding one of the first group of control constants; and the second group of control constants are determined such that when the pump current is feedback-controlled with the target voltage being switched from the first target voltage to the second target voltage, the pump current becomes stable more quickly as compared with the case where the first group of control constants continues to be used.

This gas sensor control apparatus (1) includes constant group setting means for setting a group of control constants used for the feedback control to a first group of control constants or a second group of control constants. When the target voltage is switched from the first target voltage to the second target voltage, the group of control constants are also switched from the first group of control constants to the second group of control constants.

As a result, after the target voltage is switched to the second target voltage, the pump current can be stabilized more quickly as compared with the case where the feedback control is performed such that the first group of control constants continues to be used.

Examples of the specific gas whose concentration is detected by the gas sensor include oxygen whose concentration is detected by an oxygen sensor and nitrogen oxide (NOx) whose concentration is detected by an NOx sensor.

When the concentration of oxygen is detected, preferably, the first target voltage is set to 400 mV to 500 mV. Examples of the feedback control used in the current control means include PI (proportion-integral) control and PID (proportional-integral-derivative) control.

Examples of the current control means which performs these controls include an analog computation circuit which performs analog computation, and a microprocessor and a DSP (digital signal processor) which perform digital computation.

In a preferred embodiment (2) of the above-described gas sensor control apparatus (1), the first target voltage is determined such that $H_2O$ gas contained in the gas under measurement does not substantially dissociate, and the second target voltage is higher than the first target voltage and is determined such that the $H_2O$ gas contained in the gas under measurement dissociates. The gas sensor control apparatus further comprises first current detection means for detecting, as a first pump current, the pump current flowing between the pair of second electrodes in a state in which the electromotive force cell voltage becomes equal to the first target voltage, second current detection means for detecting, as a second pump current, the pump current flowing between the pair of second electrodes in a state in which the electromotive force cell voltage becomes equal to the second target voltage, and $H_2O$ concentration detection means for detecting the concentration of the $H_2O$ gas contained in the gas under measurement on the basis of the first pump current and the second pump current.

In the gas sensor control apparatus (2), the concentration of the $H_2O$ gas contained in the gas under measurement is detected on the basis of the above-described first and second pump currents. In addition, since the group of control constants used for the feedback control is switched simultaneously with switching of the target voltage, the time required to obtain the second pump current after obtaining the first pump current is short, and the second pump current can be obtained properly. As a result, a gas sensor control apparatus can be obtained whose measurement time is short and which can properly detect the $H_2O$ gas concentration.

Notably, for detecting the $H_2O$ gas concentration, a change in the oxygen concentration of the gas under measurement which arises between the time of measurement of the first pump current and the time of measurement of the second pump current is preferably eliminated. Therefore, preferably, the $H_2O$ gas concentration is detected when the concentration of oxygen contained in the gas under measurement becomes a predetermined value; for example, when fuel cut is performed or when so-called stoichiometric control is continuously performed, for example, during a period during which a vehicle stops in an idling state.

The second target voltage is higher than the first target voltage and is determined such that the $H_2O$ gas contained in the gas under measurement dissociates. In other words, the second target voltage must be increased to a voltage at which the $H_2O$ gas contained in the gas under measurement can dissociate. However, when the second target voltage is increased excessively, the electromotive force cell (first solid electrolyte body) of the gas sensor may suffer blackening. Therefore, preferably, the second target voltage is determined to be as low as possible within a range within which the $H_2O$ gas can dissociate to a sufficient degree. Specifically, the second target voltage is preferably set to a range of 950 mV to 1100 mV.

In a preferred embodiment (3) of the above-described gas sensor control apparatus (2), the $H_2O$ concentration detection means detects the $H_2O$ gas concentration from a differential current obtained by subtracting the first pump current from the second pump current.

In the gas sensor control apparatus (3), since the $H_2O$ gas concentration is detected from the above-mentioned differential current, it is possible to properly detect the $H_2O$ gas concentration by simple processing.

In another preferred embodiment (4) of any of the above-described gas sensor control apparatuses (1) to (3), the current control means includes an analog computation circuit which performs analog computation for the feedback control on the basis of the electromotive force cell voltage; the analog computation circuit includes one or a plurality of circuit elements which determine the values of the group of control constants; and the constant group setting means includes a switch which switches the connection of the circuit elements of the analog computation circuit so as to set the group of control constants to either of the first group of control constants and the second group of control constants.

In the gas sensor control apparatus (4), the group of control constants used for the feedback control can be properly set by switching the connection of the circuit elements by means of a switch.

Notably, example methods of switching the connection of the circuit elements by the switch include a method of switching the circuit elements to be used, a method of changing the way of connecting the circuit elements together (e.g., from a series connection to a parallel connection), and a method of forming a short circuit between opposite ends of each relevant circuit element or breaking the short circuit.

In yet another preferred embodiment (5) of any of the above-described gas sensor control apparatuses (1) to (3), preferably, the current control means includes a computation section which performs digital computation for the feedback control on the basis of the electromotive force cell voltage; and the constant group setting means sets the group of control constants to either of the first group of control constants and the second group of control constants.

According to the gas sensor control apparatus (5), the group of control constants can be set properly when the current control means performs digital computation for the feedback control.

In yet another preferred embodiment (6) of any of the above-described gas sensor control apparatuses (1) to (5), the feedback control is PID control; and the group of control constants includes at least one of a proportionality constant, an integration constant, and a differentiation constant for the PID control.

According to the gas sensor control apparatus (6), the pump current can be properly controlled under the feedback control realized by PID control.

DESCRIPTION OF REFERENCE NUMERALS AND SYMBOLS

Figure 1:
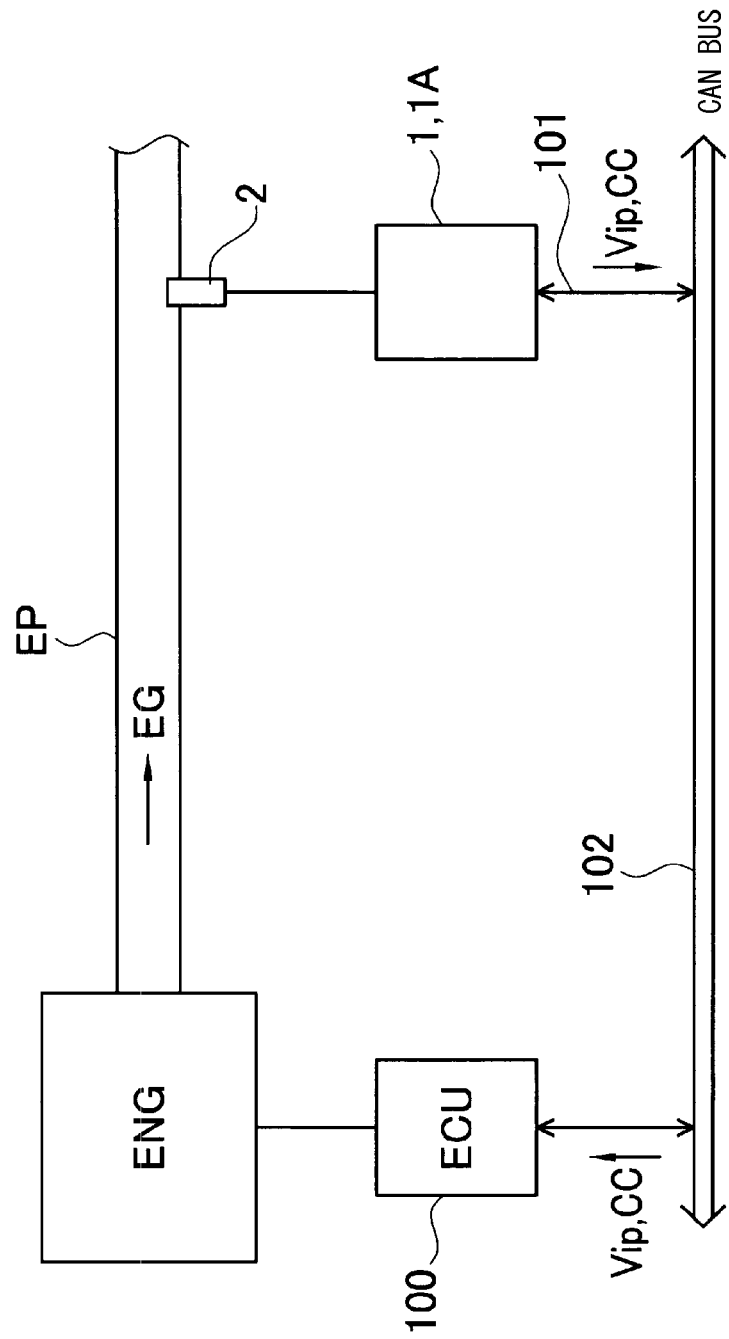
FIG. 1 is an explanatory diagram showing an overall configuration of a system in which a gas sensor and a gas sensor control apparatus according to an embodiment of the present invention are used for control of an internal combustion engine.

Reference numerals and symbols used to identify various features in the drawings include the following.
1, 1A: gas sensor control apparatus
2: gas sensor
3: sensor element section
14: pump cell
14c: electrolyte layer (second electrolyte body)
24: electromotive force cell
24c: electrolyte layer (first electrolyte body)
12, 16: electrodes (of the pump cell) (second electrodes)
22, 28: electrodes (of the electromotive force cell) (first electrodes)
Vs+, Ip+, COM: terminals (of the sensor element section)
80: heater section
Ip: pump current
Vs: electromotive force cell voltage
Vip: gas detection signal (oxygen concentration signal)
30: microprocessor
34: PWM output port
40: sensor section control circuit
59: control section (voltage setting means, constant group setting means)
61: differential amplification circuit (first current detection means, second current detection means)
69, 169: PID control circuit (current control means)
69a: first constant voltage source (voltage setting means)
69b: second constant voltage source (voltage setting means)
69e: PID computation section (analog computation circuit)
69f, 69g, 69h, 69i, 69j, 69k: circuit element groups (circuit elements)
MUX1: analog multiplexer (voltage setting means)
MUX2: analog multiplexer (constant group setting means)
R1: detection resistor (first current detection means, second current detection means)
70: heater section control circuit
ENG: internal combustion engine (engine)
EP: exhaust pipe
EG: exhaust gas (gas under measurement)
100: ECU
Vr: target voltage
Vr1: first target voltage
Vr2: second target voltage
Ip1: first pump current
Ip2: second pump current
ΔIp: differential current
CC: $H_2O$ gas concentration
Kpid: group of control constants
Kpid1: first group of control constants
Kpid2: second group of control constants
S3: first current detection means
S8: second current detection means
S5, S13: voltage setting means
S4, S12: constant group setting means
S9, S10: $H_2O$ concentration detection means

DETAILED DESCRIPTION OF THE PREFERRED EMBODIMENTS

Figure 2:
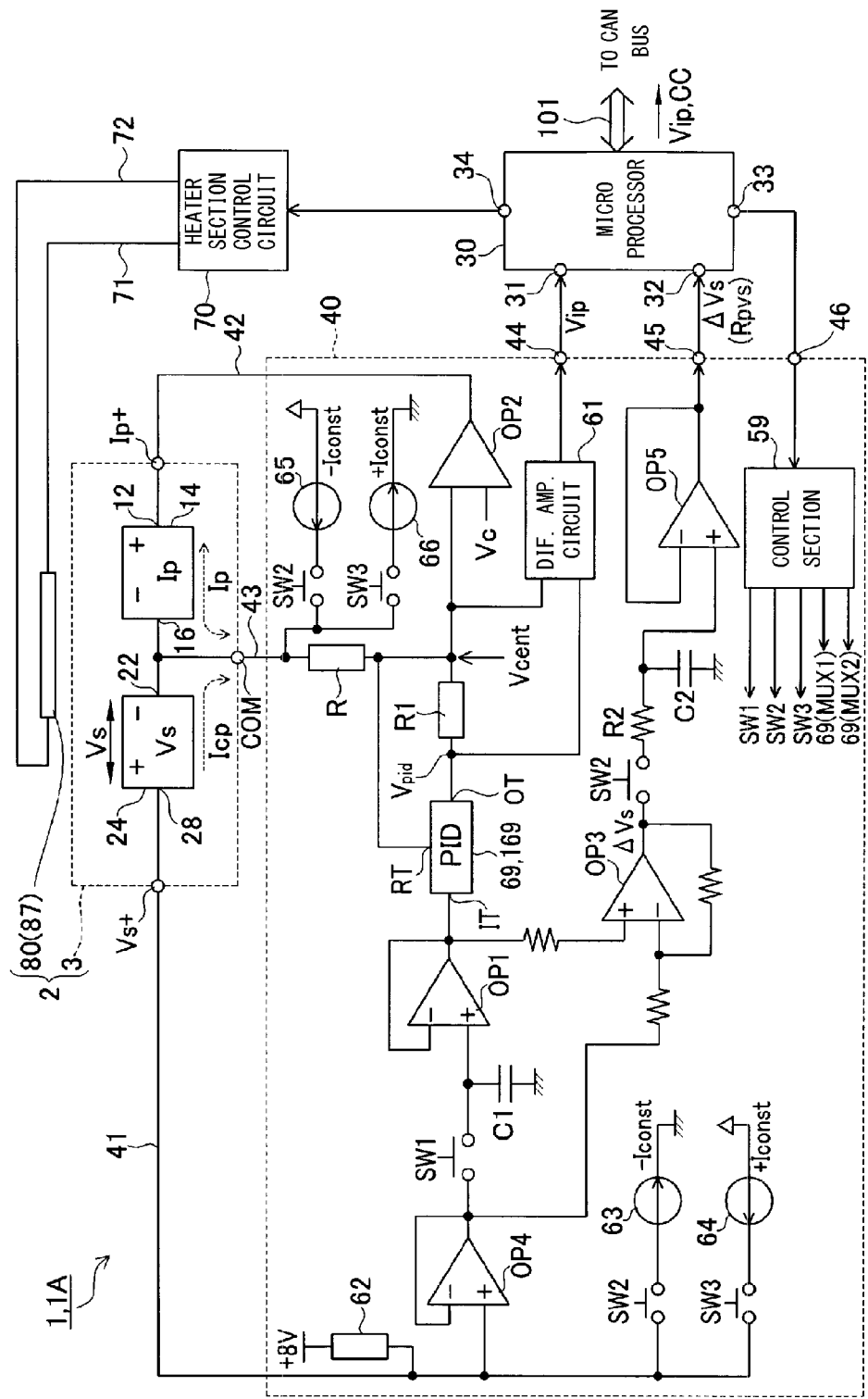
FIG. 2 is an explanatory diagram schematically showing the configuration of the gas sensor control apparatus according to the embodiment.

An embodiment of the present invention will next be described with reference to the drawings. However, the present invention should not be construed as being limited thereto. FIG. 1 is a diagram showing an overall configuration of a system in which a gas sensor control apparatus 1 according to the present embodiment and a gas sensor 2 are used for control of an internal combustion engine. FIG. 2 is a diagram schematically showing the configuration of the gas sensor control apparatus 1.

The gas sensor 2 is an air-fuel ratio sensor (full-range oxygen sensor) which is attached to an exhaust pipe EP of an internal combustion engine ENG of a vehicle (not shown) and which linearly detects the oxygen concentration (air-fuel ratio) of exhaust gas EG (gas under measurement) which is used for air-fuel ratio feedback control for the internal combustion engine ENG. As shown in FIG. 2, this gas sensor 2 includes a sensor element section 3 for detecting the oxygen concentration, and a heater section 80 for heating the sensor element section 3.

The gas sensor control apparatus 1 is connected to the gas sensor 2 and controls it. The gas sensor control apparatus 1 is also connected to a CAN (controller area network) bus 102 of the vehicle through a connection bus 101, and can exchange data with an ECU (Engine Control Unit) 100. The gas sensor control apparatus 1 includes a microprocessor 30, a sensor section control circuit 40 for controlling the sensor element section 3 of the gas sensor 2, and a heater section control circuit 70 for controlling the heater section 80.

Figure 3:
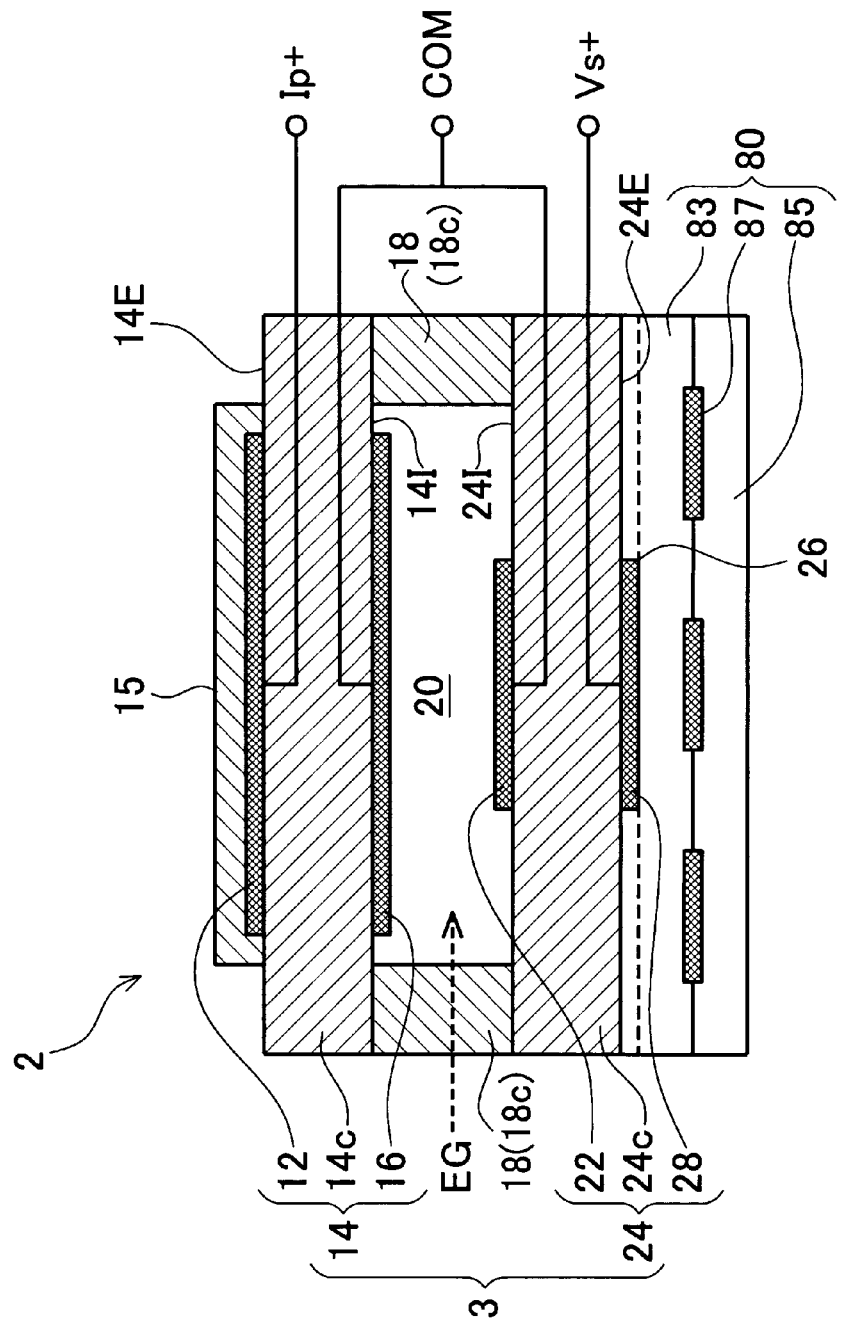
FIG. 3 is a cross-sectional view schematically showing the structure of the gas sensor.

First, the gas sensor 2 will be described. FIG. 3 is a view schematically showing the structure of the gas sensor 2. The sensor element section 3 of the gas sensor 2 is a layered sensor element formed by stacking a pump cell 14, a porous layer 18, and an electromotive force cell 24 in this sequence. The heater section 80 is further stacked on the sensor element section 3.

The pump cell 14 includes, as a substrate, an electrolyte layer 14c which is composed of a platelike solid electrolyte body mainly made of zirconia and having oxygen ion conductivity, and a pair of electrodes 12 and 16 (porous electrodes) mainly made of platinum are formed on opposite sides of the electrolyte layer 14c. Specifically, the outer electrode 12 is formed on an outer surface 14E of the electrolyte layer 14c, which surface is one surface (upper surface in FIG. 3) of the electrolyte layer 14c, and the inner electrode 16 is formed on an inner surface 141 of the electrolyte layer 14c, which surface is the other surface (lower surface in FIG. 3) of the electrolyte layer 14c.

Similarly, the electromotive force cell 24 includes, as a substrate, an electrolyte layer 24c which is composed of a platelike solid electrolyte body mainly made of zirconia and having oxygen ion conductivity, and a pair of electrodes 22 and 28 (porous electrodes) mainly made of platinum are formed on opposite sides of the electrolyte layer 24c. Specifically, the outer electrode 28 is formed on an outer surface 24E of the electrolyte layer 24c, which surface is one surface (lower surface in FIG. 3) of the electrolyte layer 24c, and the inner electrode 22 is formed on an inner surface 241 of the electrolyte layer 24c, which surface is the other surface (upper surface in FIG. 3) of the electrolyte layer 24c.

The inner surface 141 of the electrolyte layer 14c of the pump cell 14 faces the inner surface 241 of the electrolyte layer 24c of the electromotive force cell 24, and the porous layer 18 is sandwiched between the electrolyte layer 14c and the electrolyte layer 24c. The porous layer 18 has a porous wall portion 18c extending along the edge of the inner surface 141 of the electrolyte layer 14c and the edge of the inner surface 241 of the electrolyte layer 24c, and the interior of the porous layer 18 forms a hollow measurement chamber 20 which is surrounded by the porous wall portion 18c, the electrolyte layer 14c, and the electrolyte layer 24c and into which the exhaust gas EG can be introduced. Notably, the porous layer 18 restricts the flow speed of the exhaust gas EG introduced into the measurement chamber 20.

The inner electrode 16 of the pump cell 14 and the inner electrode 22 of the electromotive force cell 24 are exposed to the measurement chamber 20. These electrodes 16 and 22 are electrically connected together and are connected to a terminal COM of the sensor element section 3. The outer electrode 12 of the pump cell 14 is connected to a terminal Ip+ of the sensor element section 3, and the outer electrode 28 of the electromotive force cell 24 is connected to a terminal Vs+ of the sensor element section 3.

The outer electrode 12 of the pump cell 14 is covered with a protection layer 15 for suppressing poisoning of the outer electrode 12. The protection layer 15 is formed of porous ceramic or the like and is disposed in a flow passage through which the exhaust gas EG flows. The exhaust gas EG can reach the outer electrode 12 through the protection layer 15.

The heater section 80 is stacked on the outer surface 24E of the electrolyte layer 24c of the electromotive force cell 24 and has a structure in which a heater resistor 87 made of a conductor is sandwiched between a pair of alumina sheets 83 and 85. The electrolyte layers 14c and 24c of the sensor element section 3 are activated by increasing the temperature of the sensor element section 3 by the heater section 80. Thus, oxygen ions become able to move through the electrolyte layers 14c and 24c.

The alumina sheet 83 of the heater section 80 covers the outer electrode 28 of the electromotive force cell 24 to thereby seal the outer electrode 28. Notably, spaces (holes) within the outer electrode 28 (porous electrode) form a reference oxygen chamber 26, and function as an internal oxygen reference source as described below.

Next, the gas sensor control apparatus 1 will be described with reference to FIG. 2. The sensor section control circuit 40 is mainly constituted by an ASIC (application-specific integrated circuit), and is connected to the three terminals Vs+, Ip+, COM of the sensor element section 3 via connection paths 41, 42, 43 (specifically, wiring lines on the circuit board and lead wires). While supplying a fixed very small current Icp to the electromotive force cell 24 of the sensor element section 3, the sensor section control circuit 40 controls the pump current Ip flowing through the pump cell 14 such that the electromotive force cell voltage Vs generated between the opposite ends of the electromotive force cell 24 becomes 450 mV (=a first target voltage Vr1, described below), to thereby pump out oxygen contained in the exhaust gas EG introduced into the measurement chamber 20 through the porous layer 18 or pump oxygen into the measurement chamber 20. Since the magnitude and flow direction of the pump current Ip flowing through the pump cell 14 change with the oxygen concentration (air-fuel ratio) of the exhaust gas EG introduced into the measurement chamber 20 through the porous layer 18, the concentration of oxygen contained in the exhaust gas EG can be detected on the basis of the pump cell current Ip. Notably, the very small current Icp flows through the electromotive force cell 24 in such a direction that the oxygen within the measurement chamber 20 is pumped out to the outer electrode 28 (porous electrode). Therefore, the reference oxygen chamber 26 functions as an internal oxygen reference source.

In the sensor section control circuit 40, the magnitude of the pump current Ip is converted to a voltage signal, which is output from a gas detection signal output terminal 44 as a gas detection signal Vip. Also, in addition to the gas detection signal Vip, the sensor section control circuit 40 detects a voltage change amount ΔVs which changes in accordance with the element resistance Rpvs of the electromotive force cell 24 of the sensor element section 3, and outputs ΔVs from a voltage change amount output terminal 45. The microprocessor 30 can receive the gas detection signal Vip and the voltage change amount ΔVs via A/D input ports 31, 32. Notably, the value of the detected gas detection signal Vip is sent to the ECU 100 through the connection bus 101.

The heater section control circuit 70 is connected to the heater section 80 of the gas sensor 2 via two lead wires 71, 72, and is connected to a PWM (pulse-width-modulated) output port 34 of the microprocessor 30. The heater section control circuit 70 supplies electric current to the heater section 80, through PWM control, in accordance with PWM pulses output from the PWM output port 34.

Next, operation of the sensor section control circuit 40 for measuring the oxygen concentration using the sensor element section 3 will be described.

The terminal COM of the sensor element section 3 is connected to a Vcent point via the connection path 43 and a resistor R. The terminal Ip+ is connected to the output terminal of a second operational amplifier OP2 via the connection path 42. The terminal Vs+ is connected to the noninverting input terminal+of a fourth operational amplifier OP4 via the connection path 41. The terminal Vs+ is also connected to a constant current source circuit 62. This constant current source circuit 62 supplies the above-described fixed very small current Icp to the electromotive force cell 24.

The sensor section control circuit 40 is composed of first through fifth operational amplifiers OP1-OP5, one first switch SW1, three second switches SW2, two third switches SW3, a PID control circuit 69, a differential amplification circuit 61, current sources 63, 64, 65, 66, a control section 59, etc., as well as the above-mentioned resistor R and the constant current source circuit 62. The constant current source circuit 62, the electromotive force cell 24, and the resistor R are connected in this order through the connection paths 41, 43 to thereby form a current path through which the very small current Icp is caused to flow.

When the oxygen concentration is measured, the first switch SW1 is brought into the ON state by the control section 59. As a result, the potential at the terminal Vs+ of the sensor element section 3 is input to the input terminal IT of the PID control circuit 69 via the connection path 41 and the fourth operational amplifier OP4 and the first operational amplifier OP1, which form a voltage follower circuit. The control section 59 is a logic circuit formed within the ASIC, which constitutes the sensor section control circuit 40. The control section 59 is connected to a serial transmission port 33 of the microprocessor 30 via a command reception port 46 of the sensor section control circuit 40. In response to instructions from the microprocessor 30, the control section 59 controls the ON/OFF states of the first through third switches SW1-SW3 and performs other controls.

One input terminal of the second operational amplifier OP2 is connected to the Vcent point, and a reference voltage Vc (=+3.6 V) is applied to the other input terminal of the second operational amplifier OP2. As described above, the output terminal of the second operational amplifier OP2 is connected to the terminal Ip+ of the sensor element section 3 via the connection path 42. Notably, the Vcent point is also connected to the reference terminal RT of the PID control circuit 69.

The PID control circuit 69 has an output terminal OT in addition to the above-described input terminal IT and reference terminal RT. The PID control circuit 69 controls the magnitude of the pump current Ip by means of PID control such that a voltage difference, that is produced between the potential at the Vcent point (reference terminal RT) and the potential at the terminal Vs+ of the sensor element section 3 (input terminal IT) which is input via the fourth operational amplifier OP4 and the first operational amplifier OP1, becomes 450 mV. Specifically, the PID control circuit 69 calculates, through PID computation, the difference between a control target voltage (450 mV) and the electromotive force cell voltage Vs generated between the opposite ends of the electromotive force cell 24 (between the electrodes 28, 22), and feeds the difference back to the second operational amplifier OP2. Thus, the second operational amplifier OP2 supplies the pump current Ip to the pump cell 14.

Moreover, the sensor section control circuit 40 includes a detection resistor R1, which detects the magnitude of the pump current Ip, and converts it to a voltage signal. The voltage generated across the detection resistor R1 (the differential voltage between potentials Vcent and Vpid) is differentially amplified by the differential amplification circuit 61, and is output from the gas detection signal output terminal 44 as the gas detection signal Vip. Since the magnitude and direction of the pump current Ip change in accordance with the oxygen concentration (air-fuel ratio) as described above, the oxygen concentration can be detected from the gas detection signal Vip, which is a voltage signal representing the magnitude of the pump current Ip.

The microprocessor 30 obtains the gas detection signal (oxygen concentration signal) Vip, in the form of a digital signal, through the A/D input port 31 (i.e., through A/D conversion), and sends the obtained value to the ECU 100 via the connection bus 101.

Notably, the sensor section control circuit 40 is also used to detect a voltage change amount ΔVs which changes in accordance with the element resistance Rpvs of the electromotive force cell 24. The sensor section control circuit 40 shown in FIG. 2 includes a circuit block used for detection of the voltage change amount ΔVs. However, since the operation of the circuit block and the detail of the circuit block are disclosed in, for example, Japanese Patent Application Laid-Open (kokai) No. 2008-203190 and U.S. Pat. No. 6,120,677, incorporated herein by reference, and are well known, its description is omitted here. As described above, the voltage change amount ΔVs is output from the voltage change amount output terminal 45 of the sensor section control circuit 40 and is input to the A/D input port 32 of the microprocessor 30. The microprocessor 30 regularly detects the value of the voltage change amount ΔVs and detects the element resistance Rpvs of the electromotive force cell 24 from the voltage change amount ΔVs. The supply of electric current to the heater section 80 is feedback-controlled by the heater section control circuit 70 such that the element resistance Rpvs becomes equal to a predetermined target resistance, whereby the sensor element section 3 is heated.

Figure 4:
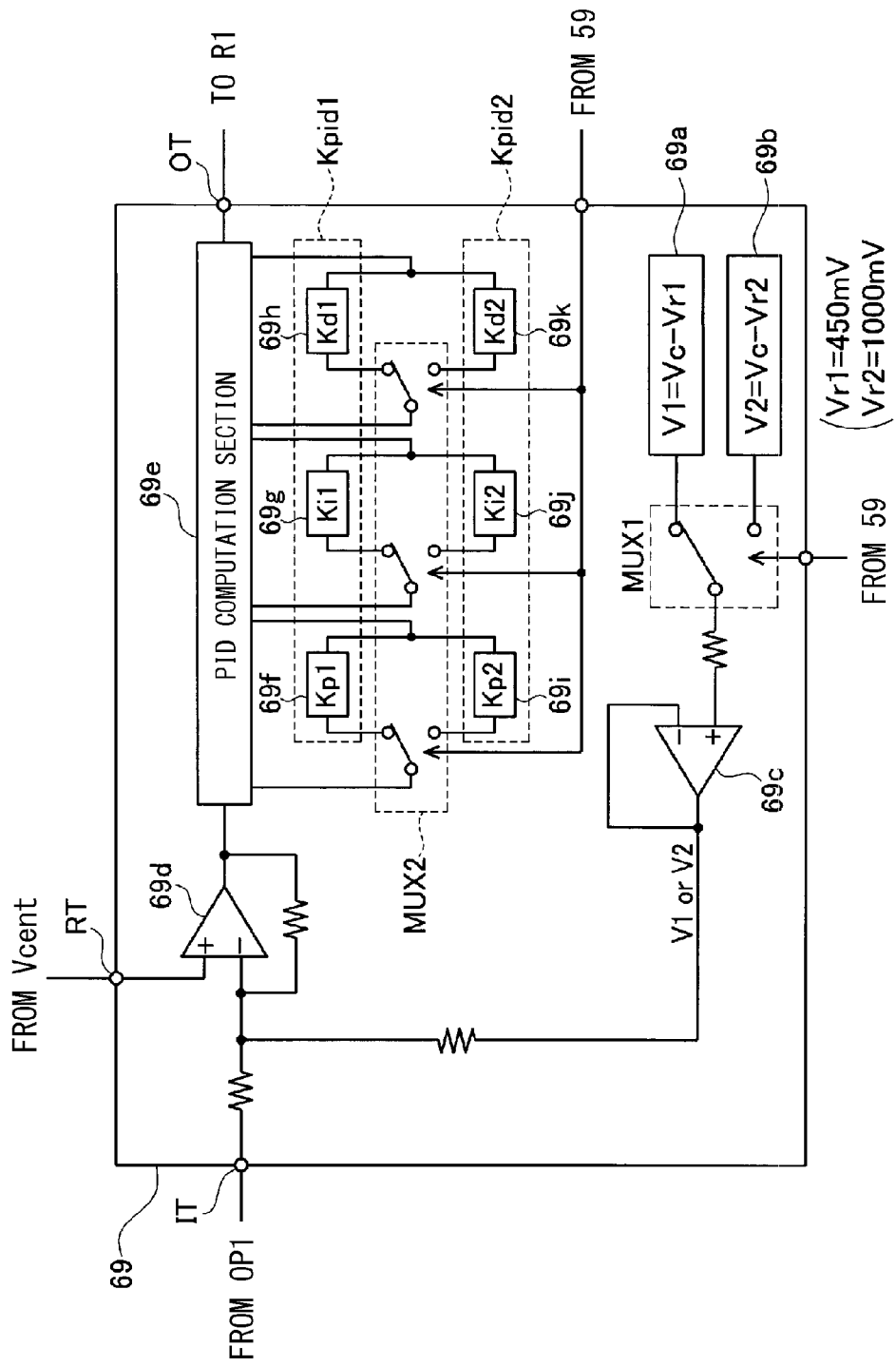
FIG. 4 is an explanatory diagram schematically showing the configuration of a PID control circuit according to the embodiment among the circuits of the gas sensor control apparatus of FIG. 2.

Next, a method of measuring the $H_2O$ gas concentration will be described using the gas sensor control apparatus 1. As described above, when the concentration of oxygen contained in the exhaust gas EG is measured, the pump current Ip is controlled such that the electromotive force cell voltage Vs becomes equal to a first target voltage Vr1 (=450 mV). In contrast, when the $H_2O$ gas concentration is measured, the pump current Ip is controlled such that the electromotive force cell voltage Vs becomes equal to a second target voltage Vr2 (=1000 mV). Namely, the electromotive force cell voltage Vs is switched from the first target voltage Vr1 (=450 mV) to the second target voltage Vr2 (=1000 mV). Specifically, as shown in FIG. 4, the PID control circuit 69 of the sensor section control circuit 40 includes a first constant voltage source 69a which outputs a first set value V1 (=Vc−Vr1) set such that the target voltage Vr of the electromotive force cell voltage Vs becomes the first target voltage Vr1 (=450 mV), and a second constant voltage source 69b which outputs a second set value V2 (=Vc−Vr2) set such that the target voltage Vr of the electromotive force cell voltage Vs becomes the second target voltage Vr2 (=1000 mV). The PID control circuit 69 is configured to switch the electromotive force cell voltage Vs between the first and second target voltages Vr1 and Vr2. More specifically, one of the outputs of the first constant voltage source 69a and the second constant voltage source 69b is input to the noninverting input terminal+of an operational amplifier 69c as a result of switching of an analog multiplexer MUX1 by the control section 59. The output of the operational amplifier 69c, which forms a voltage follower, becomes equal to the first set voltage V1 (=Vc−Vr1) or the second set voltage V2 (=Vc−Vr2). In addition, the PID control circuit 69 includes an operational amplifier 69d which amplifies the difference between the voltage at the reference terminal RT (≈Vc) and the sum of the voltage at the input terminal IT (=Vs+) and the first set voltage V1 (=Vc−Vr1) or the second set voltage V2 (=Vc−Vr2), and a PID computation section 69e which is connected to the output of the operational amplifier 69d and which performs PID computation.

Furthermore, an analog multiplexer MUX2 and circuit element groups 69f to 69k are externally connected to the PID computation section 69e of the present embodiment so as to switch the group of control constants used for feedback control of the pump current Ip. The analog multiplexer MUX2 and the circuit element groups 69f to 69k will be described in detail below. By means of these components, the pump current Ip is controlled such that the electromotive force cell voltage Vs becomes equal to the target voltage Vr which is switched between the first target voltage Vr1 (=450 mV) and the second target voltage Vr2 (=1000 mV).

The second target voltage Vr2 (=1000 mV) is a voltage determined such that not only the $O_2$ gas contained in the exhaust gas EG but also the $H_2O$ gas contained in the exhaust gas EG dissociates. Meanwhile, the first target voltage Vr1 (=450 mV) is a voltage determined such that the $H_2O$ gas contained in the exhaust gas EG does not substantially dissociate although the $O_2$ gas contained in the exhaust gas EG dissociates.

The ECU 100 issues an instruction for instructing measurement of the $H_2O$ gas concentration when a predetermined measurement start condition is satisfied; for example, when the state of supply of the exhaust gas EG (gas under measurement) to the gas sensor 2 is a state in which the exhaust gas EG continuously has a predetermined oxygen concentration (for example, when fuel cut is performed or so-called stoichiometric control is continuously performed during a period during which the vehicle stops in an idling state because, for example, the driver of the vehicle waits for a traffic light to change). The gas sensor control apparatus 1 of the present embodiment starts a measurement operation in response to this instruction. Immediately after the start of the measurement operation, the pump current Ip is controlled such that the electromotive force cell voltage Vs becomes equal to the first target voltage Vr1 because the target voltage Vr is set to the first target voltage Vr1 (=450 mV). Subsequently, in a state in which the electromotive force cell voltage Vs has become equal to the first target voltage Vr1, the pump current Ip flowing between the electrodes 12 and 16 is measured as a first pump current Ip1. Notably, as described above, the magnitude of the pump current Ip is detected by the detection resistor R1, and is output as the gas detection signal (oxygen concentration signal) Vip.

Next, the target voltage Vr is switched to the second target voltage Vr2 (=1000 mV), and the pump current Ip is controlled such that the electromotive force cell voltage Vs becomes equal to the second target voltage Vr2. In a state in which the electromotive force cell voltage Vs becomes equal to the second target voltage Vr2 after elapse of a predetermined period of time required for the electromotive force cell voltage Vs and the pump current Ip to become stable, the pump current Ip flowing between the electrodes 12 and 16 is measured as the second pump current Ip2. Notably, it is assumed that during this measurement, the oxygen concentration of the exhaust gas EG is constant; for example, the state of supply of the exhaust gas EG; i.e., the drive state of the engine (e.g., idling state) is maintained constant, whereby the air-fuel ratio is maintained at the stoichiometric air-fuel ratio.

After that, a differential current $\Delta$Ip (=Ip2−Ip1) is calculated by subtracting the first pump current Ip1 which flows as a result of dissociation of the $O_2$ gas from the second pump current Ip2. Since this differential current $\Delta$Ip is a current attributable to the dissociation of the $H_2O$ gas, the concentration of the $H_2O$ gas contained in the exhaust gas EG can be determined from the differential current $\Delta$Ip.

However, after the target voltage Vr is switched from the first voltage Vr1 (=450 mV) to the second voltage Vr2 (=1000 mV), it is necessary to wait a relatively long time (e.g., several to about 10 seconds) until the feedback-controlled pump current Ip becomes stable and it becomes possible to obtain a proper second pump current Ip2. Meanwhile, during a period during which the $H_2O$ gas concentration is detected, the oxygen concentration cannot be detected. Therefore, in engine control, feedback control of the air-fuel ratio which is performed using the oxygen concentration output (air-fuel ratio output) of the gas sensor cannot be performed during this period, and the air-fuel ratio is subject to open-loop control. Therefore, there is a need to shorten, to the extent possible, the time required for properly detecting the $H_2O$ gas concentration.

In view of this, in the gas sensor control apparatus 1 of the present embodiment, when the target voltage Vr is switched from the first voltage Vr1 (=450 mV) to the second voltage Vr2 (=1000 mV), the group of control constants used for the feedback control of the pump current Ip is switched in the PID computation section 69e of the PID control circuit 69 so as to quickly stabilize the pump current Ip. As shown in FIG. 4, the analog multiplexer MUX2 and the circuit element groups 69f to 69k each including a resistor and a capacitor (not shown) are externally connected to the PID computation section 69e of the PID control circuit 69. The PID computation section 69e is mainly composed of an unillustrated operational amplifier and forms, together with the external circuit element groups 69f to 69k, an analog computation circuit which performs analog computation for PID feedback control.

The circuit element groups 69f, 69g, and 69h set the values of the control constants used for the PID computation performed in the PID computation section 69e (i.e., a proportionality constant Kp, an integration constant Ki, and a differentiation constant Kd) to Kp1, Ki1, and Kd1 (hereinafter these constants will be referred to as the "first group of control constants Kpid1"). Meanwhile, the circuit element groups 69i, 69j, and 69k set the values of the control constants used for the PID computation performed in the PID computation section 69e (i.e., the proportionality constant Kp, the integration constant Ki, and the differentiation constant Kd) to Kp2, Ki2, and Kd2 (hereinafter these constants will be referred to as the "second group of control constants Kpid2"), which differ from Kp1, Ki1, and Kd1, respectively. The circuit element group 69f and the circuit element group 69i, the circuit element group 69g and the circuit element group 69j, and the circuit element group 69h and the circuit element group 69k form respective pairs and are connected to the analog multiplexer MUX2. As a result of the internal switches of the analog multiplexer MUX2 being simultaneously switched by the control section 59, the first group of control constants Kpid1 or the second group of control constants Kpid2 are used as the group of control constants Kpid in the PID control circuit 69. Notably, when the second group of control constants Kpid2 are used as the group of control constants Kpid, the pump current Ip becomes stable more quickly as compared with the case where the first group of control constants Kpid1 continues to be used. Therefore, in the present embodiment, when the target voltage Vr is the first target voltage Vr1, the group of control constants Kpid are set to the first group of control constants Kpid1, and when the target voltage Vr is the second target voltage Vr2, the group of control constants Kpid are set to the second group of control constants Kpid2.

Notably, in the present embodiment, the values of Kp2, Ki2, and Kd2 of the second group of control constants Kpid2 differ from the values of Kp1, Ki1, and Kd1 of the first group of control constants Kpid1. However, the values of Kp2, Ki2, and Kd2 of the second group of control constants Kpid2 may be freely determined so long as when the pump current Ip is feedback-controlled with the target voltage Vr being switched from the first target voltage Vr1 to the second target voltage Vr2, the pump current Ip becomes stable more quickly as compared with the case where the first group of control constants Kpid1 continues to be used. In order to satisfy this requirement, it is sufficient for one of the control constants, i.e., the proportionality constant Kp, the integration constant Ki, and the differentiation constant Kd, of the second group of control constants Kpid2 to differ from the first group of control constants Kpid1.

As stated in the specification, examples of the feedback control used in the current control means include PI (proportion-integral) control and PID (proportional-integral-derivative) control. When switching the group of control constants from the first group of control constants to the second group of control constants, each constant value of proportion (P), integration (I) and derivative (D) can be appropriately changed in consideration of frequency properties of a gas sensor.

Examples of the second group of control constants may include a value that any one of the constants forming the first group of control constants is increased. For example, when the feedback control is PID control, at least a value of any one of P, I, D constants (more particularly, proportionality constant) is made large in order to form the second group of control constants.

Alternatively, when the feedback control is PID control, the second group of control constants may be formed such that values of proportionality constant and differentiation constant in P, I, D constants forming the first group of control constants are made large, while a value of integral constant is made small.

As described above, in the gas sensor control apparatus 1 of the present embodiment, when the $H_2O$ gas concentration is detected, simultaneously with the switching of the target voltage Vr from the first target voltage Vr1 to the second target voltage Vr2, the group of control constants Kpid of the PID control circuit 69 (PID computation section 69e) used for the feedback control of the pump current Ip are switched from the first group of control constants Kpid1 to the second group of control constants Kpid2.

As a result, after the target voltage Vr is switched to the second target voltage Vr2, the pump current Ip can be stabilized more quickly as compared with the case where the first group of control constants Kpid1 continues to be used.

Next, operation of the gas sensor control apparatus 1 (particularly, the microprocessor 30) according to the present embodiment will be described with reference to the flowchart of FIG. 5.

Figure 5:
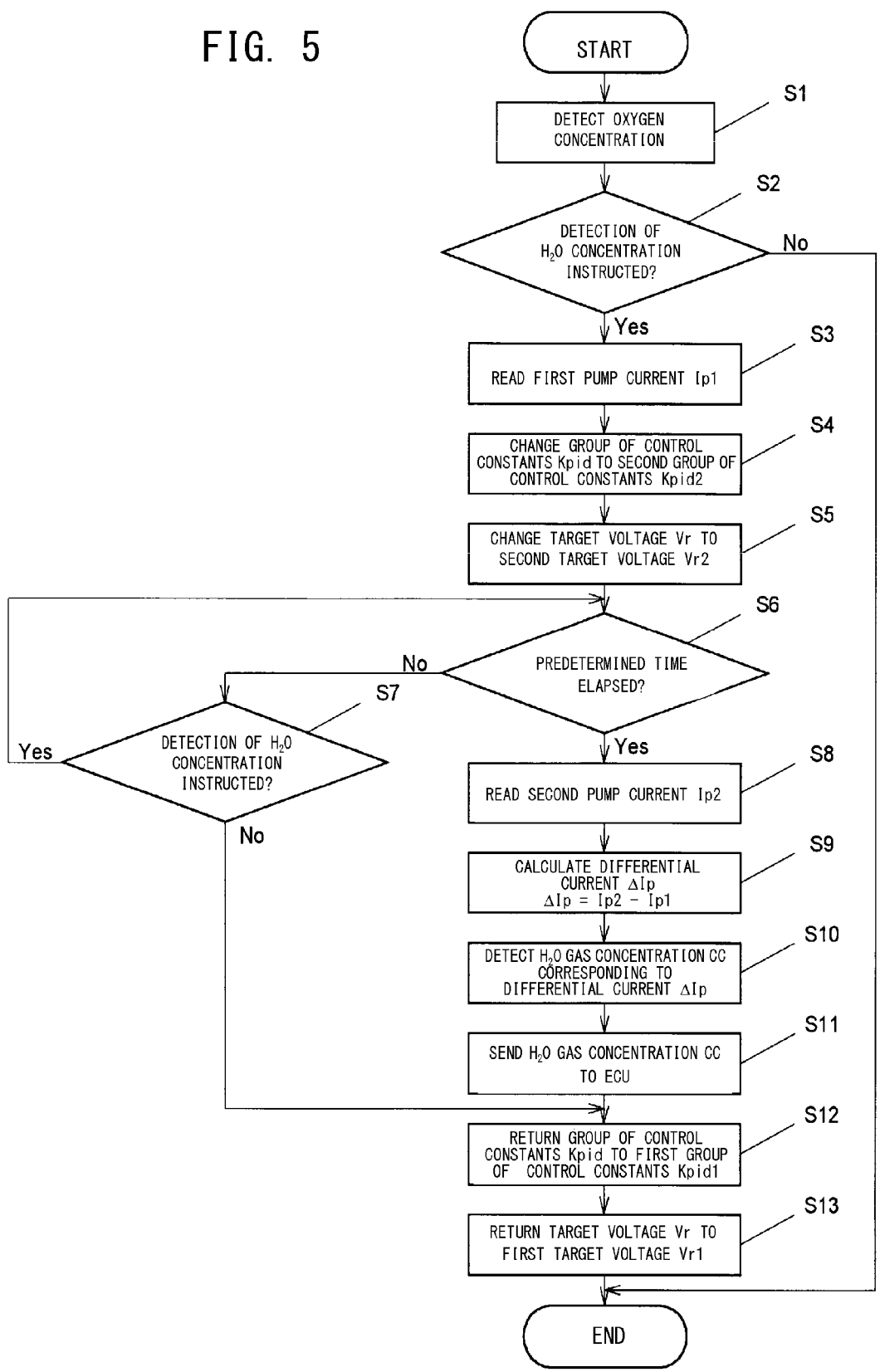
FIG. 5 is a flowchart showing the processing operation of a microprocessor of the gas sensor control apparatus according to the embodiment.

The microprocessor 30 of the gas sensor control apparatus 1 periodically performs the main processing shown in FIG. 5 every time a predetermined timing comes so as to detect the oxygen concentration. When detection of the $H_2O$ gas concentration is instructed by the ECU 100, the microprocessor 30 performs the processing for detecting the $H_2O$ gas concentration.

When the microprocessor 30 starts the main processing upon arrival of the predetermined timing, the microprocessor 30 first detects the oxygen concentration in step S1. Notably, at this time, in the PID control circuit 69 of the sensor section control circuit 40, the target voltage Vr of the electromotive force cell voltage Vs is the first target voltage Vr1 (=450 mV). Therefore, the pump current Ip is controlled such that the electromotive force cell voltage Vs becomes equal to the first target voltage Vr1. Also, the group of control constants Kpid of the PID control circuit 69 (PID computation section 69e) used for the feedback control of the pump current Ip is set to the first group of control constants Kpid1. The magnitude of the pump current Ip at this time is detected as the gas detection signal (oxygen concentration signal) Vip.

In subsequent step S2, the microprocessor 30 determines whether or not it receives a detection instruction which instructs detection of the $H_2O$ gas concentration and which is output from the ECU 100 when the predetermined measurement start condition is satisfied (e.g., when fuel cut is performed or the vehicle stops in an idling state). In the case where the microprocessor 30 does not receive the detection instruction (No), the microprocessor 30 ends the present main processing without performing any processing. Namely, the microprocessor 30 performs only detection of the oxygen concentration in step S1. Meanwhile, in the case where the microprocessor 30 receives the detection instruction which instructs detection of the $H_2O$ gas concentration (Yes), the microprocessor 30 proceeds to step S3.

In step S3, the microprocessor 30 sets the target voltage Vr to the first target voltage Vr1 (=450 mV), reads, as the first pump current Ip1, the magnitude of the pump current Ip (gas detection signal Vip) at the time when the electromotive force cell voltage Vs becomes equal to the first target voltage Vr1, and stores the first pump current Ip1. Next, in step S4, the microprocessor 30 switches the group of control constants Kpid from the first group of control constants Kpid1 to the second group of control constants Kpid2 before changing the target voltage Vr in step S5. Specifically, the microprocessor 30 switches the analog multiplexer MUX2 through the control section 59 such that in place of the circuit element groups 69f, 69g, and 69h, the circuit element groups 69i, 69j, and 69k are used in the PID computation section 69e. Next, in step S5, the microprocessor 30 switches the target voltage Vr to the second target voltage Vr2 (=1000 mV). Specifically, the microprocessor 30 switches the analog multiplexer MUX1 through the control section 59 such that in place of the first constant voltage source 69a, the second constant voltage source 69b is connected to the operational amplifier 69c. In step S6 subsequent thereto, the microprocessor 30 determines whether or not a predetermined period of time has elapsed after switching of the target voltage Vr in step S5. The predetermined period of time is a period of time required for the electromotive force cell voltage Vs and the pump current Ip to become stable. In the case where the predetermined period of time has not yet elapsed (No), the microprocessor 30 proceeds to step S7.

In step S7, the microprocessor 30 determines whether or not the $H_2O$ gas concentration detection instruction output from the ECU 100 in step S2 still continues. In the case where the detection instruction continues (Yes), the microprocessor 30 returns to step S6 and waits for the elapse of the predetermined period of time while repeating steps S6 and S7. In the case where the predetermined period of time has elapsed, the microprocessor 30 makes a "Yes" determination in step S6 and proceeds to step S8. Meanwhile, in the case where the detection instruction from the ECU 100 is discontinued while waiting for the elapse of the predetermined period of time, the microprocessor 30 makes a "No" determination in step S7 and proceeds to step S12.

Notably, as a result of switching of the group of control constants Kpid to the second group of control constants Kpid2 in step S4, the pump current Ip becomes stable more quickly as compared with the case where the feedback control is performed while the first group of control constants Kpid1 continues to be used independent of the target voltage. Therefore, the predetermined period of time in step S6 is set to be shorter than the case where the first group of control constants Kpid1 continues to be used.

In step S8, the microprocessor 30 reads, as the second pump current Ip2, the magnitude of the pump current Ip (gas detection signal Vip) at the time when the electromotive force cell voltage Vs becomes equal to the second target voltage Vr2 (=1000 mV) and stores the second pump current Ip2.

In step S9 subsequent thereto, the microprocessor 30 calculates the differential current ΔIp (ΔIp=Ip2−Ip1). In step S10 subsequent thereto, the microprocessor 30 obtains a $H_2O$ gas concentration CC corresponding to the obtained differential current ΔIp with reference to a table which shows the relation between the differential current ΔIp and the $H_2O$ gas concentration CC. In step S11 subsequent thereto, the microprocessor 30 sends the detected $H_2O$ gas concentration CC to the ECU 100 via the connection bus 101.

Next, in step S12, the microprocessor 30 returns the group of control constants Kpid to the first group of control constants Kpid1. Specifically, the microprocessor 30 switches the analog multiplexer MUX2 through the control section 59 such that in place of the circuit element groups 69i, 69j, and 69k, the circuit element groups 69f, 69g, and 69h are used in the PID computation section 69e. Furthermore, in step S13 subsequent thereto, the microprocessor 30 returns the target voltage Vr to the first target voltage Vr1 (=450 mV). Specifically, the microprocessor 30 switches the analog multiplexer MUX1 through the control section 59 such that in place of the second constant voltage source 69b, the first constant voltage source 69a is connected to the operational amplifier 69c. After completing step S13, the microprocessor 30 ends the present main processing. Notably, when the microprocessor 30 makes a "No" determination in step S7, the microprocessor 30 ends the present main processing after executing steps S12 and S13.

In the present embodiment, the electrodes 22 and 28 of the electromotive force cell 24 correspond to the pair of first electrodes, and the electrodes 12 and 16 of the pump cell 14 correspond to the pair of second electrodes of the invention. The electrolyte layer 24c of the electromotive force cell 24 corresponds to the first solid electrolyte body, and the electrolyte layer 14c of the pump cell 14 corresponds to the second solid electrolyte body of the invention.

The PID control circuit 69 of the sensor section control circuit 40 corresponds to the current control means of the invention. The detection resistor R1 of the sensor section control circuit 40, the differential amplification circuit 61 of the sensor section control circuit 40, and the microprocessor 30 which executes step S3 correspond to the first current detection means of the invention. The detection resistor R1 of the sensor section control circuit 40, the differential amplification circuit 61 of the sensor section control circuit 40, and the microprocessor 30 which executes step S8 correspond to the second current detection means of the invention. The first constant voltage source 69a, the second constant voltage source 69b, and the analog multiplexer MUX1 of the PID control circuit 69 of the sensor section control circuit 40, the control section 59, and the microprocessor 30 which executes steps S5 and S13 correspond to the voltage setting means of the invention.

The PID computation section 69e of the PID control circuit 69 corresponds to the analog computation circuit of the invention which performs analog computation for feedback control. The analog multiplexer MUX2 corresponds to the switch of the invention for switching the connection of the circuit element groups 69f to 69k. The analog multiplexer MUX2, the control section 59, and the microprocessor 30 which executes steps S4 and S12 correspond to the constant group setting means of the invention.

The microprocessor 30 which executes steps S9 and S10 corresponds to the $H_2O$ gas concentration detection means of the invention.

As described above, the gas sensor control apparatus 1 of the present embodiment includes the constant group setting means (step S4, S12) which sets the group of control constants Kpid used for feedback control of the pump current Ip to the first group of control constants Kpid1 or the second group of control constants Kpid2. When the target voltage Vr is switched from the first target voltage Vr1 to the second target voltage (step S5), the group of control constants Kpid are also switched from the first group of control constants Kpid1 to the second group of control constants Kpid2 (step S4).

As a result, after the target voltage Vr is switched to the second target voltage Vr2, the pump current Ip can be stabilized more quickly as compared with the case where the first group of control constants Kpid1 continues to be used. Namely, as a result of switching from the first to the second group of control constants, the predetermined period of time in step S6 can be set to a shorter period of time.

In the gas sensor control apparatus 1 of the present embodiment, the $H_2O$ gas concentration of the gas under measurement is detected on the basis of the first pump current Ip1 and the second pump current Ip2. In addition, since the group of control constants Kpid used for feedback control of the pump current Ip are changed simultaneously with the changing of the target voltage Vr, the time required to obtain the second pump current Ip2 after obtaining the first pump current Ip1 is short, and the second pump current Ip2 can be obtained properly. As a result, a gas sensor control apparatus 1 can be obtained whose measurement time is short and which can properly detect the $H_2O$ gas concentration.

In the gas sensor control apparatus 1 of the present embodiment, since the $H_2O$ gas concentration is detected using the differential current $\Delta Ip$ (=Ip2−Ip1), the $H_2O$ gas concentration can be properly detected through simple processing.

In the gas sensor control apparatus 1 of the present embodiment, the group of control constants Kpid used for feedback control can be properly switched between the first group of control constants Kpid1 and the second group of control constants Kpid2 by switching the connection of the circuit element groups 69f to 69k by the analog multiplexer MUX2.

According to the gas sensor control apparatus 1 of the present embodiment, the pump current Ip can be properly controlled under feedback control realized by PID control of the PID control circuit 69.

(Modification)

Next, a gas sensor control apparatus 1A according to a modification of the above-described embodiment will be described. In the gas sensor control apparatus 1 of the above-described embodiment, the PID control circuit 69 of the sensor section control circuit 40 includes a PID computation section 69e, which is an analog computation circuit, as shown in FIG. 4, and the switching between the first group of control constants Kpid1 and the second group of control constants Kpid2 is performed by switching the connection of the circuit element groups 69f to 69k by the analog multiplexer MUX2.

Figure 6:
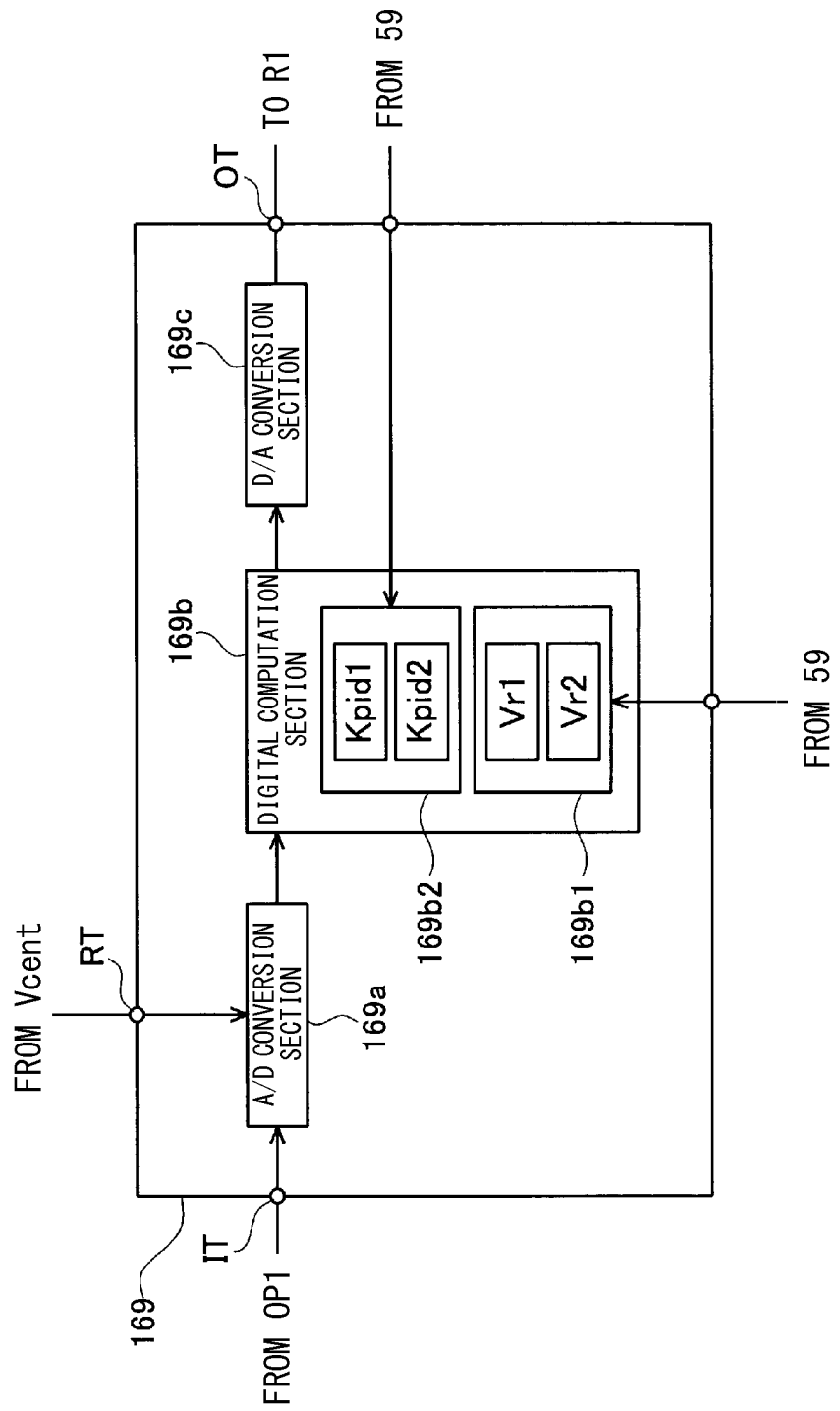
FIG. 6 is an explanatory diagram schematically showing the configuration of a PID control circuit according to a modification among the circuits of the gas sensor control apparatus of FIG. 2.

In contrast, in the gas sensor control apparatus 1A of the present modification, the sensor section control circuit 40 includes a PID control circuit 169 in place of the PID control circuit 69 formed by an analog computation circuit. The PID control circuit 169 is formed by a DSP (digital signal processor) which includes a digital computation section 169b shown in FIG. 6. Namely, in the present modification, an ASIC which includes a DSP for forming the PID control circuit 169 is used for the sensor section control circuit 40.

The PID control circuit 169 includes an A/D conversion section 169a and a D/A conversion section 169c in addition to the digital computation section 169b. The potentials at the reference terminal RT and the input terminal IT are converted to digital values by the A/D converter 169a and are input to the digital computation section 169b. The digital computation section 169b includes a voltage setting section 169b1 which sets, as the target voltage Vr, a digital value corresponding to either of the first target voltage Vr1 and the second target voltage Vr2 in response to an instruction from the control section 59; and a constant group setting section 169b2 which sets, as the group of control constants Kpid, the digital values corresponding to either of the first group of control constants Kpid1 and the second group of control constants Kpid2 in response to an instruction from the control section 59. The digital computation section 169b performs digital computation for the feedback control (PID control) by using these digital values, and outputs the result of the computation (in the form of a digital value) to the D/A conversion section 169c. The D/A conversion section 169c converts the digital value output from the digital computation section 169b to an analog voltage, and outputs it from the output terminal OT. The portions of the sensor section control circuit 40 other than the PID control circuit 169 perform the same processing operations as those in the embodiment shown in FIG. 2. The remaining portion has the same configuration as that of the embodiment, and the microprocessor 30 performs the same operation as that of the embodiment shown by the flowchart of FIG. 5. Therefore, their descriptions are omitted.

In the present modification, the PID control circuit 169 corresponds to the current control means of the invention. The voltage setting section 169b1, the control section 59, and the microprocessor 30 which executes steps S5 and S13 correspond to the voltage setting means of the invention.

The digital computation section 169b of the PID control circuit 169 corresponds to the computation section of the invention which performs digital computation for feedback control. The constant group setting section 169b2, the control section 59, and the microprocessor 30 which executes steps S4 and S12 correspond to the constant group setting means of the invention.

In the gas sensor control apparatus 1A of the present modification, the constant group setting section 169b2 is provided in the digital computation section 169*b*, and as in the case of the embodiment, the group of control constants Kpid is also switched from the first group of control constants Kpid1 to the second group of control constants Kpid2 when the target voltage Vr is switched from the first target voltage Vr1 to the second target voltage Vr2.

As a result, after the target voltage Vr is switched to the second target voltage Vr2, the pump current Ip can be stabilized more quickly as compared with the case where the first group of control constants Kpid1 continues to be used.

According to the gas sensor control apparatus 1A of the present modification, when digital computation for feedback control is performed, the group of control constants Kpid can be properly set by the constant group setting section 169*b*2 of the digital computation section 169*b*.

According to the gas sensor control apparatus 1A of the present modification, the pump current Ip can be properly controlled under feedback control realized by PID control of the PID control circuit 169.

In the above, the gas sensor control apparatus of the present invention has been described on the basis of the gas sensor control apparatus 1 according to the embodiment and the gas sensor control apparatus 1A according to the modification. However, needless to say, the present invention is not limited to the embodiment and modification, and can be modified freely without departing from the scope of the invention.

For example, in the embodiment and the modification, the gas sensor 2 is an oxygen sensor for detecting the oxygen concentration (air-fuel ratio) of exhaust gas EG. However, the "gas sensor" is not limited to the oxygen sensor, and may be an NOx sensor for detecting the concentration of nitrogen oxide (NOx), or the like.

Also, the gas sensor is not limited to those attached to the exhaust pipe, and the present invention may be applied to a gas sensor which is attached to the intake pipe of an engine having an EGR device and which detects the concentration of oxygen contained in intake gas.

In the embodiment, all of the proportionality constant Kp, the integration constant Ki, and the differentiation constant Kd are switched. However, only a portion of the group of control constants may be switched. For example, of the control constants, only the proportionality constant Kp may be switched or only the proportionality constant Kp and the integration constant Ki may be switched. Also, the embodiment may be modified such that control means other than PI control and PID control is employed and the control constants used by the control means are switched.

In the embodiment, the circuit element groups (69*f* and 69*i*, 69*g* and 69*j*, 69*h* and 69*k*) to be used are switched by the analog multiplexer MUX2. However, the embodiment may be configured such that the way of connection between circuit elements connected together is changed, or a short circuit is formed between opposite ends of each relevant circuit element or broken.

In the modification, an ASIC which includes a DSP for forming the PID control circuit 169 is used for the sensor section control circuit 40, and digital computation for feedback control is performed by the DSP incorporated in the ASIC. However, such digital computation may be performed by a microprocessor or a dedicated digital computation circuit which is provided separately from the ASIC.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2012-125403 filed May 31, 2012, incorporated herein by reference in its entirety.

What is claimed is:

1. A gas sensor control apparatus for detecting the concentration of a specific gas contained in a gas under measurement using a gas sensor which includes an electromotive force cell having an oxygen ion conductive first solid electrolyte body and a pair of first electrodes formed on the first solid electrolyte body, and a pump cell having an oxygen ion conductive second solid electrolyte body and a pair of second electrodes formed on the second solid electrolyte body, the gas sensor control apparatus comprising:

current control means for feedback-controlling pump current flowing between the pair of second electrodes such that an electromotive force cell voltage produced between the pair of first electrode becomes equal to a target voltage;

voltage setting means for setting the target voltage to either of a first target voltage when the concentration of the specific gas is detected and a second target voltage different from the first target voltage; and constant group setting means for setting a group of control constants used for the feedback control to a first group of control constants when the target voltage is the first target voltage and to a second group of control constants when the target voltage is the second target voltage, wherein at least one of the second group of control constants differs from a corresponding one of the first group of control constants;

the second group of control constants are determined such that when the pump current is feedback-controlled with the target voltage being switched from the first target voltage to the second target voltage, the pump current becomes stable more quickly as compared with the case where the first group of control constants continues to be used;

the constant group setting means switches the control constants to the second group from the first group before the voltage setting means changes the target voltage to the second target voltage from the first target voltage;

the first target voltage is determined such that $H_2O$ gas contained in the gas under measurement does not substantially dissociate;

the second target voltage is higher than the first target voltage and is determined such that the $H_2O$ gas contained in the gas under measurement dissociates; and the gas sensor control apparatus further comprises:

first current detection means for detecting, as a first pump current, the pump current flowing between the pair of second electrodes in a state in which the electromotive force cell voltage becomes equal to the first target voltage, second current detection means for detecting, as a second pump current, the pump current flowing between the pair of second electrodes in a state in which the electromotive force cell voltage becomes equal to the second target voltage, and $H_2O$ concentration detection means for detecting the concentration of the $H_2O$ gas contained in the gas under measurement on the basis of the first pump current and the second pump current.

2. The gas sensor control apparatus as claimed in claim 1, wherein the $H_2O$ concentration detection means detects the $H_2O$ gas concentration from a differential current obtained by subtracting the first pump current from the second pump current.

3. A gas sensor control apparatus as claimed in claim 1, wherein
- the current control means includes an analog computation circuit which performs analog computation for the feedback control on the basis of the electromotive force cell voltage;
- the analog computation circuit includes one or a plurality of circuit elements which determine the values of the group of control constants; and
- the constant group setting means includes a switch which switches the connection of the circuit elements of the analog computation circuit so as to set the group of control constants to either of the first group of control constants and the second group of control constants.

4. The gas sensor control apparatus as claimed in claim 1, wherein
- the current control means includes a computation section which performs digital computation for the feedback control on the basis of the electromotive force cell voltage; and
- the constant group setting means sets the group of control constants to either of the first group of control constants and the second group of control constants.

5. The gas sensor control apparatus as claimed in claim 1, wherein
- the feedback control is PID (proportional-integral-derivative) control; and
- the group of control constants includes at least one of a proportionality constant, an integration constant, and a differentiation constant for the PID control.

* * * * *